US012788351B2

(12) United States Patent
Kroenke-Hille et al.

(10) Patent No.: US 12,788,351 B2
(45) Date of Patent: Nov. 10, 2026

(54) ASSISTING SUBJECT POSITIONING IN MEDICAL IMAGING

(71) Applicant: KONINKLIJKE PHILIPS N.V., Eindhoven (NL)

(72) Inventors: Sven Kroenke-Hille, Hamburg (DE); Jens Von Berg, Hamburg (DE); Stewart Matthew Young, Hamburg (DE); Daniel Bystrov, Hamburg (DE); Heiner Matthias Brueck, Pinneberg (DE); Andre Goossen, Eldena (DE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 211 days.

(21) Appl. No.: 18/710,659

(22) PCT Filed: Nov. 21, 2022

(86) PCT No.: PCT/EP2022/082527
§ 371 (c)(1),
(2) Date: May 16, 2024

(87) PCT Pub. No.: WO2023/099247
PCT Pub. Date: Jun. 8, 2023

(65) Prior Publication Data

US 2025/0032063 A1 Jan. 30, 2025

(30) Foreign Application Priority Data

Nov. 30, 2021 (EP) .................................... 21211277

(51) Int. Cl.
*A61B 6/00* (2024.01)
*A61B 6/04* (2006.01)
(Continued)

(52) U.S. Cl.
CPC ............ *A61B 6/545* (2013.01); *A61B 6/0492* (2013.01); *A61B 6/505* (2013.01); *A61B 6/5217* (2013.01);
(Continued)

(58) Field of Classification Search
None
See application file for complete search history.

(56) References Cited

U.S. PATENT DOCUMENTS

2007/0225596 A1 9/2007 Iustin
2009/0079576 A1 3/2009 Yankelevitz
(Continued)

FOREIGN PATENT DOCUMENTS

JP 2017536860 A 12/2017
WO WO-2016184704 A1 * 11/2016 ............... A61B 6/04

OTHER PUBLICATIONS

PCT International Search Report, International application No. PCT/EP2022/082527, Feb. 22, 2023.

*Primary Examiner* — David Ometz
(74) *Attorney, Agent, or Firm* — Larry Liberchuk

(57) ABSTRACT

A computer-implemented method for assisting positioning of a subject having an implant in X-ray imaging includes receiving X-ray image data of the subject including the implant and receiving exam request data indicating at least an exam type to be performed for the implant. At least one set of image features assigned to the requested exam type and indicative of positioning of the subject and/or the implant relative to an X-ray imaging device is determined. Image content of the received X-ray image data is analyzed for the determined set of image features. Based on the analysis, feedback indicative of positioning the subject and the X-ray imaging device relative to each other with respect to a target positioning is determined.

15 Claims, 2 Drawing Sheets

(51) Int. Cl.
*A61B 6/50* (2024.01)
*G06T 7/73* (2017.01)

(52) U.S. Cl.
CPC ...... *G06T 7/73* (2017.01); *G06T 2207/30008* (2013.01); *G06T 2207/30052* (2013.01)

(56) References Cited

U.S. PATENT DOCUMENTS

| | | | | |
|---|---|---|---|---|
| 2017/0100089 | A1 | 4/2017 | Chang | |
| 2017/0205477 | A1 | 7/2017 | Grodzki | |
| 2018/0247427 | A1 | 8/2018 | Geiger | |
| 2018/0318012 | A1 | 11/2018 | Blau | |
| 2019/0066260 | A1* | 2/2019 | Suehling ................ | A61B 6/461 |
| 2019/0183439 | A1 | 6/2019 | Joerger | |
| 2019/0318497 | A1 | 10/2019 | Zhao | |
| 2019/0380806 | A1* | 12/2019 | Spahn .................. | A61N 5/1049 |
| 2020/0375546 | A1 | 12/2020 | Shoudy | |
| 2020/0405194 | A1 | 12/2020 | Sekine | |
| 2021/0007806 | A1* | 1/2021 | Karade .................. | A61B 34/10 |
| 2024/0070867 | A1 | 2/2024 | Kronke | |

* cited by examiner

ASSISTING SUBJECT POSITIONING IN MEDICAL IMAGING

FIELD OF THE INVENTION

The present invention relates to medical imaging, and in particular to a computer-implemented method for assisting positioning of a subject having an implant in X-ray imaging, to a system for assisting positioning of a subject having an implant in X-ray imaging, and to a computer program element for performing the method and/or to control the system.

BACKGROUND OF THE INVENTION

In medical imaging, e.g. in X-ray imaging, appropriate subject positioning can be regarded as being crucial for achieving X-ray images, e.g. musculoskeletal X-ray images etc., of diagnostic quality due to the projective nature of this image modality.

This applies in particular if the positioning of an orthopedic implant is to be imaged, since even slight mispositioning of the subject can render an X-ray image, with respect to its quality, particularly in terms of the achieved projection, non-diagnostic. This can mitigate the X-ray image suitability for e.g. assessing the implant placement after e.g. a surgery or monitoring possible movements of the implant with respect to the bone over time.

SUMMARY OF THE INVENTION

There may, therefore, be a need for improved means for at least assisting positioning of a subject in a manner allowing acquiring a medical image with a desired positioning of an implant therein. The invention is defined by the independent claims, while advantageous embodiments are defined by the dependent claims.

According to a first aspect, there is provided a computer-implemented method for assisting positioning of a subject having an implant in X-ray imaging. The method comprises the steps of receiving X-ray image data of the subject including the implant, receiving exam request data indicating at least an exam type to be performed for the specific implant, and determining at least one set of image features being assigned to the requested exam type and indicative for positioning of the subject and/or the implant relative to an X-ray imaging device, analyzing an image content of the received X-ray image data for the determined set of image features; and determining, from the analysis of the image content, a feedback being indicative for positioning the subject and the X-ray imaging device to each other with respect to a target positioning, to be provided for assisting the positioning. Advantageously, the set of image features defines at least a contour of the implant, and the contour is determined to meet a corresponding target contour defined by the set of image features in case of meeting the target positioning.

In this way, given an acquired X-ray image of an orthopedic implant, the above method allows the subject positioning to be assessed and to give a feedback, e.g. a confirmation that the positioning is already correct or a recommendation, i.e. an action instruction, for improving the positioning if e.g. a retake is necessary. The method and system disclosed herein provides an automatic assessment of the subject implant positioning relative to the X-ray imaging device, so that assessing a diagnostic quality of the X-ray image can be automatically assessed in order to improve image quality and/or diagnostic quality, patient throughput, and time management in particular, for a novice operator, such as a radiographer. Further, due to improved computer-aided positioning, individual subjective measures are objectified by standardizing image quality, e.g. across a department, a medical imaging facility or the like. Further, given that the subject-positioning of the current image deviates from a target positioning, the above method allows the operator, e.g. radiographer, to determine appropriate actions which could improve the image quality.

As used herein, the X-ray image data may comprise one or more X-ray images acquired by utilizing the X-ray imaging device, wherein the one or more X-ray images are of a region of interest of the subject where the implant is located.

Further, as used herein, the exam type to be performed may be indicative for e.g. a specific type of projection view of a specific region or anatomy of interest of the subject. For example, the exam type may be indicative for a knee anteroposterior view, which is a standard projection to assess the knee joint, distal femur, proximal tibia and fibula and the patella, or other views associated with regions where an implant may be present. By way of example, in a knee anteroposterior view, the subject may be positioned supine on a table with the knee and ankle joint in contact with the table, wherein its leg is extended, and the knee is not rotated. The type of exam is not limited herein and may extend to various other exam types of different regions, joints, or the like, and/or different implant types.

As used herein, the at least one set of image features being assigned to the requested exam type may be related to one or more image-quality criteria, such as flatness of a proximal plateau of the implant, symmetric appearance of condyles, or the like. For example, the at least one set of image features may be indicative for such a flatness, symmetric appearance, or the like. For at least one set of image features may be automatically measured within the image using a processor and/or a computational model or the like.

As used herein, the positioning of the subject may include determining and/or providing a specific pose and/or posture relative to the X-ray imaging device, e.g. the X-ray tube, or vice versa. Accordingly, the feedback, which may be output graphically, e.g. via a display etc., via audio, e.g. via a loudspeaker, headphone, etc., or the like, may indicate how the positioning of the subject is to be changed to comply with a target or desired positioning.

Further, as used herein providing the feedback may comprise communicating it to the operator via e.g. a communication interface and/or user interface, with a confirmation that the positioning is already correct or one or more action instructions such as "rotate the leg by 10° about the tibial axis", "slightly rotate the foot to the left", or the like.

According to an embodiment, the set of image features may be analyzed with respect to their appearance in case of the target positioning. For example, the positioning, e.g. the positioning quality or accuracy, may be quantified by comparing the detected features, within the analysis, to their appearance in the case of an ideal and/or target positioning with respect to one or more measurements of e.g. the mean curvature of an implant's plateau, a contour distance between the medial and lateral condyle after horizontally flipping one of them and rigidly registering it to the other one, or the like. If a deviation from the ideal or target positioning in these measurements can be assigned to different positioning degrees of freedom, e.g. leg rotation or the like, a recommendation, i.e. action instruction, for correcting mispositioning can be communicated to the operator. In this way, the image data may be automatically assessed by using computational means.

In an embodiment, analyzing the image content may comprise, preferably automatically, measuring the set of image features to determine compliance with and/or deviation from the target positioning. In this way, the image data may be automatically assessed by using computational means.

According to an embodiment, the set of image features may comprise one or more geometric parameters and/or features to be measured within the image content. Geometric parameters and/or features can be easily determined within the image data by image analysis, for example by an appropriate computer program executed by a processor or the like. In this way, the image data may be automatically assessed by using computational means.

In an embodiment, the one or more geometric parameters may define one or more of a straight line, a curved line, a curve, and a polygon. These geometric parameters can be determined, for example, on a pixel and/or voxel basis and, if necessary, can also be determined and measured by inserting auxiliary parameters, such as a line, a curve, etc. In this way, the image data may be automatically assessed by using computational means.

According to an embodiment, the set of image features may define a contour of the implant and/or tissue being adjacent to and/or surrounding the implant, and wherein the contour is determined to meet a corresponding target contour defined by the set of image features in case of meeting the target positioning. For example, it may be measured, within the image data, a mean curvature of the implant's plateau, a contour distance between the medial and lateral condyle after horizontally flipping one of them and rigidly registering it to the other one, or the like. In this way, the image data may be automatically assessed by using computational means.

In an embodiment, analyzing the image content may comprise determining symmetry properties of sections of the implant and/or the tissue to each other based on the set of set of image features. For example, the symmetric appearance of e.g. condyles may be measured. In this way, the image data may be automatically assessed by using computational means.

According to an embodiment, the set of image features may be fed into a 3D anatomy model of the anatomy of interest configured to estimate a 3D pose and/or posture of the region or anatomy of interest, e.g. a joint or the like, and/or the implant, preferably with respect to the 3D anatomy model, wherein the feedback is determined based on the 3D anatomy model. For example, the 3D anatomy model may be utilized to estimate and/or reconstruct a part of or a full acquisition geometry. In this way, the image data may be automatically assessed by using computational means.

In an embodiment, during analyzing the image content, a first subset of image features may comprise one or more geometric parameters for measuring and evaluating and a second subset of image features may be assigned to the 3D anatomy model, and the evaluated measured first subset of image features may be combined with the parametrized 3D anatomy model. For example, the 3D anatomy model may be used to estimate the 3D pose and/or posture of the region or anatomy of interest and/or the implant based on the second subset of image features, while the first subset of image features is used for measurement as described above. In this way, the positioning can be determined by combining the estimation of the 3D pose and/or posture and the measurements within the image data allows the accuracy of determining the positioning to be further improved.

According to an embodiment, during analyzing the image content, the set of image features is fed into a 3D implant model being similar to or of the implant and being configured to estimate a 3D pose and/or posture of the implant. For example, the 3D implant model may be assigned to a specific implant type that at least largely corresponds to the implant type of the subject to be imaged. The 3D implant model may be provided as e.g. a 3D CAD-model. Thereby, the 3D implant model may be deformable to be adapted to the implant actually present in the given subject to be imaged. Optionally, the 3D implant model may be of the implant actually present in the given subject. In this way, the relative positioning of the implant within the subject can be reconstructed, which might vary from case to case and might be the actual objective of this exam, e.g. assessment of orthopedic surgery.

In an embodiment, the set of image features may comprise one or more landmarks configured to detect the implant. In this way, the implant can be detected based on the one or more landmarks detected within the X-ray image data.

According to an embodiment, wherein a relative position of the implant to the subject's tissue is recorded. For example, the examination, i.e., image acquisition of the region or anatomy of interest may be performed repeatedly, with the relative position of each examination recorded and used for the assessment of orthopedic surgery. E.g. a change in the relative position of implant and surrounding tissue, e.g. bone(s), can be derived from assessing the recorded relative positions.

The above method may preferably be performed by use of a system according to the second aspect. Further, the method steps may be implemented in hardware and/or software.

According to a second aspect, there is provided a system for assisting positioning of a subject having an implant in X-ray imaging. The system is configured to carry out the method according to the first aspect.

The device comprises a processor, which is configured to receive X-ray image data of the subject including the implant, receive exam request data indicating at least an exam type to be performed for the specific implant, and determining at least one set of image features being assigned to the requested exam type and indicative for positioning of the subject and/or the implant relative to an X-ray imaging device. Further, the processor is configured to analyze an image content of the received X-ray image data for the determined set of image features, and determine, from the analysis of the image content, a feedback being indicative for positioning the subject and the X-ray imaging device to each other with respect to a target positioning, to be provided for assisting the positioning.

In this way, given an acquired X-ray image of an orthopedic implant, the above system allows the subject positioning to be assessed and to give a recommendation, i.e. the action instruction, for improving the positioning if e.g. a retake is necessary.

According to an embodiment, further comprising a communication and/or user interface configured to output the feedback for e.g. an operator. For example, the communication interface may be configured to provide the feedback, and optionally action instruction, graphically, in audio, or the like. It may comprise or may connected to a display, loudspeaker, or the like. In this way, the system may improve positioning of the subject with a feedback, which may also include a precise instruction to guide positioning.

According to a third aspect, there is provided a computer program element, which when executed by a processor is configured to carry out the method of the first aspect, and/or to control a system according to the second aspect.

According to a fourth aspect, there is provided a computer-readable storage or transmission medium, which has stored, or which carries the computer program element according to the third aspect.

It is noted that the above embodiments may be combined with each other irrespective of the aspect involved. Accordingly, the method may be combined with structural features of the device and/or system of the other aspects and, likewise, the system may be combined with features described above with regard to the method.

These and other aspects of the present invention will become apparent from and elucidated with reference to the embodiments described hereinafter.

BRIEF DESCRIPTION OF THE DRAWINGS

Exemplary embodiments of the invention will be illustrated in the following drawings.

DETAILED DESCRIPTION OF EMBODIMENTS

Figure 1:
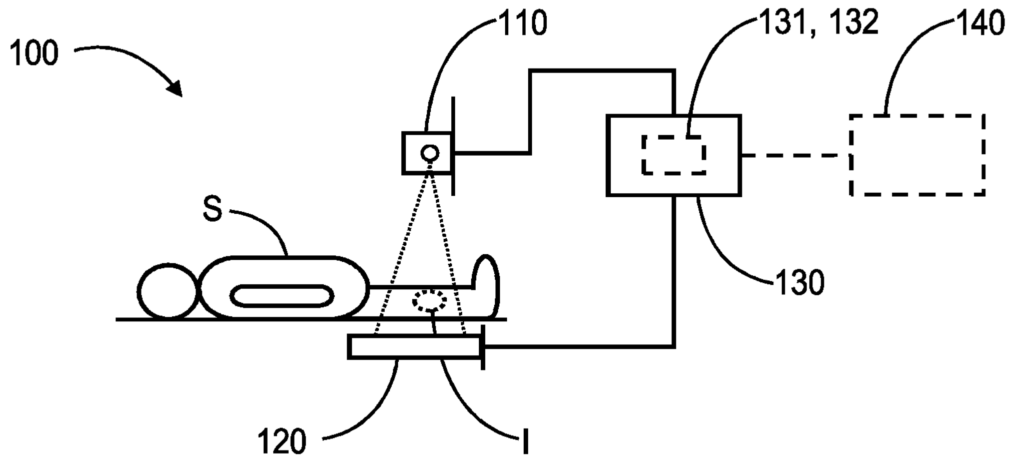
FIG. 1 shows in a schematic block diagram a system for assisting positioning of a subject having an implant in X-ray imaging, according to an embodiment.

FIG. 1 shows in a schematic block diagram a system 100 that is configured to assist positioning of a subject S having an implant I in X-ray imaging, the latter being carried out by using, for example, an X-Ray device with a radiation source 110 and a detector 120. Further, the device 100 comprises a processor 130) and, optionally, a communication interface and/or user interface 140.

The processor 130 is configured to receive X-ray image data of the subject including the implant from the X-ray device. For example, as shown in FIG. 1, the X-ray device is used to acquire an image from the subject's S knee, in which the subject S has the implant I.

Further, the processor 130 is configured to receive exam request data that indicates at least an exam type to be performed for the specific implant I and/or subject S. For example, the exam type indicates a specific type of projection view of a specific region or anatomy of interest of the subject. For example, the exam type may be indicative for a knee anteroposterior view, which is a standard projection to assess the knee joint, distal femur, proximal tibia and fibula and the patella, or other views associated with regions where the implant may be present.

The processor 130 is further configured to determine at least one set of image features that is assigned to the requested exam type and that is indicative for positioning of the subject and/or the implant relative to an X-ray imaging device. Thereby, the set of image features is analyzed with respect to their appearance in case of a target positioning, which is desired for the specific exam type. Further, the processor may be configured to choose an appropriate set of image-quality criteria, such as flatness of the proximal plateau of the implant and symmetric appearance of the condyles, or the like, wherein the at least one set of image features may be assigned to the set of image-quality criteria.

Further, the processor 130 is configured to analyze an image content of the received X-ray image data for the determined set of image features. This can be done automatically, e.g. by means of image analysis technique, image recognition technique, image manipulation technique, etc. For example, for analyzing the image content of the received X-ray image data, the processor 130 may be configured to utilize a convolutional neural network, which is trained for this purpose. Further, analyzing the image content may comprise detecting one or more landmarks or one or more contours. Thereby, analyzing the image content comprises determining, e.g. measuring, comparing etc., the set of image features to determine compliance with and/or deviation from the target positioning.

The processor 130 is further configured to determine, from the analysis of the image content, a feedback being indicative for positioning the subject and the X-ray imaging device to each other towards a target positioning, to be provided for assisting the positioning. By way of example, the actual positioning, i.e. the actual positioning quality, is quantified by comparing the detected features to their appearance in the case of the target positioning, i.e. an ideal positioning for the specific examination type, the implant type, etc., with respect to one or more corresponding target values, e.g. a mean curvature of a plateau of the implant I, a contour distance between the medial and lateral condyle after horizontally flipping one of them and rigidly registering it to the other one, or the like.

For example, the set of image features comprises one or more geometric parameters to be measured within the image content. The processor 130 may perform image analysis to identify the set of image features, where these are specified as geometric parameters and determined, e.g. measured, as such within the X-ray image data. By way of example, the one or more geometric parameters define one or more of a straight line, a curved line, a curve, and a polygon. For and/or with these parameters, for example, distances between points, lines, centerlines, curves, etc. can be measured to infer the image quality, and also whether it meets or matches the set of image-quality criteria associated with the corresponding exam type.

By way of example, the set of image features define a contour of the implant I and/or tissue being adjacent to and/or surrounding the implant I. Thereby, the contour is analyzed to determine whether it meets or matches a corresponding target contour defined by the set of image features for the target positioning. For example, it may be determined whether the contour appears flat within the X-ray image data, which flatness may be at least on indicator that the actual positioning corresponds to the target positioning or not. It is conceivable that a flat contour is to be expected in a projection with a target positioning.

Further, by way of example, the image content may be analyzed to determine one or more symmetry properties of sections of the implant I and/or tissue to each other based on the set of set of image features. Thereby, it is determined whether the symmetry meets or matches a corresponding target symmetry defined by the set of image features for the target positioning. The symmetry may comprise, for example, symmetry of the condyles, i.e. symmetric appearance of the condyles, or other distinctive tissue.

Optionally, the processor 130 is configured to feed the set of image features into a 3D anatomy model 131 of the anatomy of interest configured to estimate a 3D pose and/or posture, wherein the feedback is determined based on the 3D anatomy model.

Further optionally, the processor 130 is configured to use a first subset of image features that comprises one or more geometric parameters for measuring and evaluating and to use a second subset of image features that is assigned to the 3D anatomy model 131, and to combine the evaluated measured first subset of image features with the parametrized 3D anatomy model 131, in order to determine the positioning of the subject S and/or implant I. For example, the first subset of image features may be directly related to the set of image-quality criteria for the specific exam type, and the second subset of image features may be only implicitly related to the image-quality criteria but predictive for the 3D pose and/or posture of the anatomy or tissue, e.g. bone tissue, such as a joint, and/or of the implant.

Optionally, the processor 130 is configured to feed the set of image features into a 3D implant model 132, which is similar to or specific for the implant I and configured to estimate a 3D pose and/or posture of the implant I.

Further optionally, the set of image features comprise one or more landmarks configured to detect the implant I.

Optionally, the processor 130 is further configured to determine and/or record a relative position of the implant I to the subject's S tissue, e.g. to monitor and/or assess any changes after e.g. an orthopedic surgery.

The communication interface 140 is configured to output the feedback. For example, the communication interface 140 may be configured to provide the feedback graphically, in audio, or the like, or may provide a corresponding signal to a remote device (not shown). The communication interface 140) may comprise or may be connected to a display, loudspeaker, or the like.

Figures 2A, 2B:
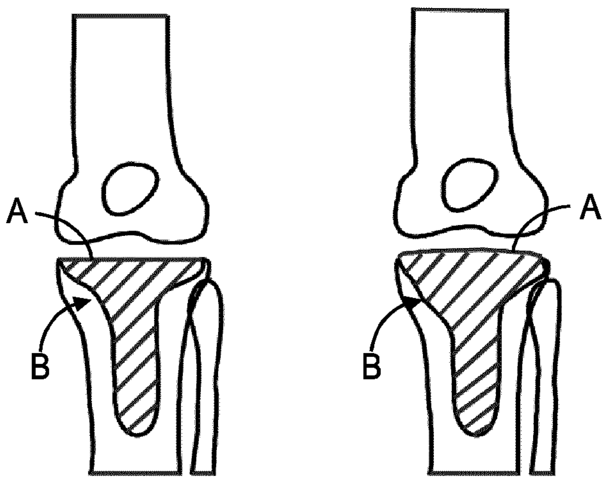
FIG. 2A illustrates schematically an impact of subject positioning on diagnostic quality of an exemplary knee anteroposterior view X-ray image with a target positioning.
FIG. 2B illustrates schematically an impact of subject positioning on diagnostic quality of an exemplary knee anteroposterior view X-ray image with a deviation from a target positioning.

Referring now to FIGS. 2A and 2B, which illustrate the impact of positioning subject S and/or implant I relative to the X-ray imaging device, it will be explained in more detail how processor 130 analyzes the X-ray image data.

Thereby, FIG. 2A illustrates schematically the impact of subject positioning on diagnostic quality of an exemplary knee anteroposterior view X-ray image with a target positioning, meaning an ideal positioning in which the tibial plateau of the implant is visible as a straight line such that the implant's cementation can be properly assessed. As illustrated in FIG. 2A, at a section A, the plateau is rather flat, which is recognizable in the image by corresponding image features and/or geometric parameters. Further, at a section B, the condyles are rather symmetrical.

Further, FIG. 2B illustrates schematically the impact of subject positioning on diagnostic quality of an exemplary knee anteroposterior view X-ray image with a deviation from the target positioning, meaning a mispositioning caused by a rotation about the medio-lateral axis resulting in a curved appearance of the tibial plateau of the implant such that the state of the bone cement just beneath the tibial plateau cannot be assessed. As illustrated in FIG. 2B, at section A, the plateau is not flat but rather curved, which is recognizable in the image by corresponding image features and/or geometric parameters. Further, at section B, the condyles are rather unsymmetrical.

Figure 3:
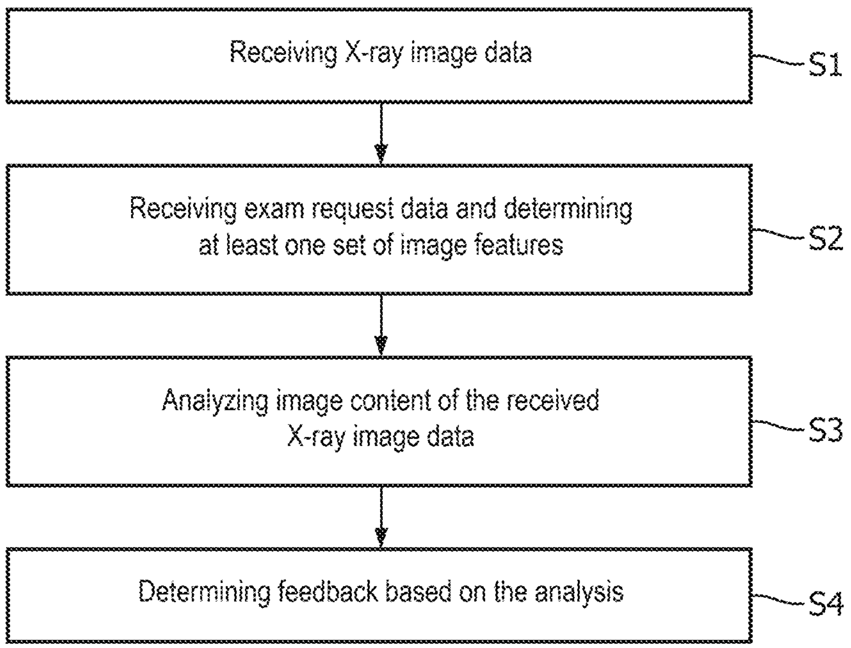
FIG. 3 shows in a flow chart a method for assisting positioning of a subject having an implant in X-ray imaging, according to an embodiment.

FIG. 3 shows in a flow diagram a method for assisting positioning of a subject having an implant in X-ray imaging. The method is carried out by utilizing the system 100 described above.

In a step S1, e.g. by the processor 130, X-ray image data of the subject S including the implant I is received. preferably from the X-ray imaging device.

In a step S2, e.g. by the processor 130, exam request data indicating at least an exam type to be performed for the specific implant may be received, and at least one set of image features being assigned to the requested exam type and indicative for positioning of the subject and/or the implant relative to the X-ray imaging device may be determined. That is, the set of image features, which may relate to a set of image-quality criteria for the specific exam type, may be determined based on the received exam request data. Advantageously, the set of image features defines at least a contour of the implant, and the contour is determined to meet a corresponding target contour defined by the set of image features in case of meeting the target positioning.

In a step S3, e.g. by the processor 130, an image content of the received X-ray image data is analyzed for the determined set of image features. For example, this analysis may comprise image analysis, image recognition, image manipulation, segmentation of the image content, or the like.

In a step S4, e.g. by the processor 130, from the analysis of the image content, a feedback being indicative for positioning the subject and the X-ray imaging device to each other with respect to a target positioning is determined, to be provided for assisting the positioning.

In another exemplary embodiment, a computer program or computer program element is provided that is characterized by being configured to execute the method steps of the method according to one of the preceding embodiments, on the system 100.

The computer program element might therefore be stored to be executed by the processor 130, which might also be part of an embodiment. This processor unit may be configured to perform or induce performing of the steps of the method described above. Moreover, it may be configured to operate the components of the above-described device and/or system. The computing unit can be configured to operate automatically and/or to execute the orders of a user. A computer program may be loaded into a working memory of a data processor. The data processor may thus be equipped to carry out the method according to one of the preceding embodiments.

Further, the computer program element might be able to provide all necessary steps to fulfill the procedure of an exemplary embodiment of the method as described above.

According to a further exemplary embodiment of the present invention, a computer readable medium, such as a CD-ROM, USB stick or the like, is presented wherein the computer readable medium has a computer program element stored on it which computer program element is described by the preceding section.

The computer program element may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It is noted that embodiments of the invention are described with reference to different subject matters. In particular, some embodiments are described with reference to method type claims whereas other embodiments are described with reference to the device or system type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and the foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

LIST OF REFERENCE SIGNS

100 system
110 radiation source
120 detector
130 processor
131 3D anatomy model
132 3D implant model
140 communication and/or user interface
I implant
S subject
S1 receive X-ray image data of the subject including the implant
S2 receive exam request data indicating at least an exam type to be performed for the specific implant, and determine at least one set of image features being assigned to the requested exam type and indicative for positioning of the subject relative to an X-ray imaging device
S3 analyze an image content of the received X-ray image data for the determined set of image features
S4 determine from the analysis of the image content, a feedback indicative for positioning the subject and the X-ray imaging device to each other with respect to a target positioning, to be provided for assisting the positioning

The invention claimed is:

1. A computer-implemented method for assisting positioning of a subject having an implant in X-ray imaging, the method comprising:

receiving X-ray image data of the subject including the implant;

receiving exam request data indicating at least an exam type to be performed for the specific implant, and determining at least one set of image features being assigned to the requested exam type and indicative for positioning of the subject relative to an X-ray imaging device;

analyzing an image content of the received X-ray image data for the determined set of image features; and determining, from the analysis of the image content, a feedback being indicative for positioning the subject and the X-ray imaging device to each other with respect to a target positioning, to be provided for assisting the positioning, wherein the set of image features defines at least a contour of the implant, and wherein the contour is determined to meet a corresponding target contour defined by the set of image features in case of meeting the target positioning.

2. The method according to claim 1, wherein the set of image features is analyzed with respect to appearance in case of the target positioning.

3. The method according to claim 1, wherein analyzing the image content comprises measuring the set of image features to determine compliance with and/or deviation from the target positioning.

4. The method according to claim 1, wherein the set of image features comprises one or more geometric parameters to be measured within the image content.

5. The method according to claim 4, wherein the one or more geometric parameters define one or more of a straight line, a curved line, a curve, and a polygon.

6. The method according to claim 1, wherein the set of image features define a contour of tissue being adjacent to and/or surrounding the implant, and wherein the contour is determined to meet a corresponding target contour defined by the set of image features in case of meeting the target positioning.

7. The method according to claim 1, wherein analyzing the image content comprises determining symmetry properties of sections of the implant and/or tissue to each other based on the set of image features.

8. The method according to claim 1, wherein, during analyzing the image content, the set of image features is fed into a 3D implant model being similar to the implant and being configured to estimate a 3D pose and/or posture of the implant.

9. The method according to claim 1, wherein the set of image features is fed into a 3D anatomy model of the anatomy of interest configured to estimate a 3D pose and/or a posture, wherein the feedback is determined based on the 3D anatomy model.

10. The method according to claim 9, wherein, during analyzing the image content, a first subset of image features comprises one or more geometric parameters for measuring and evaluating and a second subset of image features is assigned to the 3D anatomy model, and the evaluated measured first subset of image features is combined with the 3D anatomy model.

11. The method according to claim 10, wherein the set of image features comprise one or more landmarks configured to detect the implant.

12. The method according to claim 1, wherein a relative position of the implant to the subject's tissue is recorded.

13. A system for assisting positioning of a subject having an implant in X-ray imaging, the system comprising:

a memory that stores a plurality of instructions; and a processor coupled to the memory and configured to execute the plurality of instructions to carry out a method comprising:

receiving X-ray image data of the subject including the implant;

receiving exam request data indicating at least an exam type to be performed for the specific implant, and determining at least one set of image features being assigned to the requested exam type and indicative for positioning of the subject relative to an X-ray imaging device;

analyzing an image content of the received X-ray image data for the determined set of image features; and determining, from the analysis of the image content, a feedback being indicative for positioning the subject and the X-ray imaging device to each other with respect to a target positioning, to be provided for assisting the positioning, wherein the set of image features defines at least a contour of the implant, and wherein the contour is determined to meet a corresponding target contour defined by the set of image features in case of meeting the target positioning.

14. The system of claim 13, further comprising a communication interface configured to output the feedback.

15. A non-transitory computer-readable medium comprising executable instructions which, when executed by at least one processor, cause the at least one processor to perform a method for assisting positioning of a subject having an implant in X-ray imaging, the method comprising:

receiving X-ray image data of the subject including the implant;

receiving exam request data indicating at least an exam type to be performed for the specific implant, and determining at least one set of image features being assigned to the requested exam type and indicative for positioning of the subject relative to an X-ray imaging device;

analyzing an image content of the received X-ray image data for the determined set of image features; and determining, from the analysis of the image content, a feedback being indicative for positioning the subject and the X-ray imaging device to each other with respect to a target positioning, to be provided for assisting the positioning, wherein the set of image features defines at least a contour of the implant, and wherein the contour is determined to meet a corresponding target contour defined by the set of image features in case of meeting the target positioning.

* * * * *